US006777576B2

United States Patent
Ikemoto et al.

(10) Patent No.: US 6,777,576 B2
(45) Date of Patent: Aug. 17, 2004

(54) PRODUCTION METHOD OF 2-CYCLOHEXYL-2-HYDROXY-2-PHENYLACETIC ACID INTERMEDIATE THEREFOR AND PRODUCTION METHOD THEREOF

(75) Inventors: Tetsuya Ikemoto, Osaka (JP); Wei-Guo Gao, Osaka (JP); Mitsuhiro Takeda, Osaka (JP); Masami Igi, Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/992,167

(22) Filed: Nov. 6, 2001

(65) Prior Publication Data

US 2003/0013911 A1 Jan. 16, 2003

(30) Foreign Application Priority Data

Nov. 7, 2000 (JP) ........................................ 2000-339437

(51) Int. Cl.[7] .............................................. C07C 59/40
(52) U.S. Cl. .......................... 562/468; 560/55; 562/405
(58) Field of Search .................................. 562/468, 405, 562/402; 560/55, 40, 42

(56) References Cited

U.S. PATENT DOCUMENTS

| 2,884,426 A | 4/1959 | Kottler et al. |
|---|---|---|
| 5,973,182 A | 10/1999 | Bakale et al. |
| 6,025,177 A | 2/2000 | Senanayake et al. |
| 6,090,971 A | 7/2000 | Bakale et al. |

FOREIGN PATENT DOCUMENTS

| EP | 0 913 393 A2 | 5/1999 |
|---|---|---|
| EP | 1205464 | * 5/2002 |
| JP | 11 193271 | 7/1999 |
| WO | WO 00/23414 A2 | 4/2000 |
| WO | WO 00/27786 A1 | 5/2000 |
| WO | WO 00/27786 | * 5/2000 |

OTHER PUBLICATIONS

Clerici et al, Tetrahedron (1986) vol. 42 (2) pp. 561–572.*
Boeckman, Jr. et al., "Alkoxy Enediolates," *J. Org. Chem.*, 42 (17), 2948–2950 (1977).
Visser et al., "Stereoselective Synthesis and Biodistribution of Potent [$^{11}$C]–Labeled Antagonists for Positron Emission Tomography Imaging of Muscarinic Receptors in the Airways," *Journal of Medicinal Chemistry*, 40 (1), 117–124 (1977).

* cited by examiner

*Primary Examiner*—Rita Desai
*Assistant Examiner*—Hector M Reyes
(74) *Attorney, Agent, or Firm*—Leydig, Voit & Mayer, Ltd.

(57) ABSTRACT

The present invention relates to production of 2-cyclohexyl-2-hydroxy-2-phenylacetic acid useful as an intermediate for pharmaceutical products, by an industrial means, economically, safely in a good yield. Novel 2-(2'-cyclohexen-1'-yl)-2-hydroxy-2-phenylacetic acid ester obtained by reacting cyclohexene and benzoylformic acid ester in the presence of a Lewis acid is hydrolyzed and reduced to give 2-cyclohexyl-2-hydroxy-2-phenylacetic acid.

26 Claims, No Drawings

PRODUCTION METHOD OF 2-CYCLOHEXYL-2-HYDROXY-2-PHENYLACETIC ACID INTERMEDIATE THEREFOR AND PRODUCTION METHOD THEREOF

TECHNICAL FIELD OF THE INVENTION

The present invention relates to a production method of 2-cyclohexyl-2-hydroxy-2-phenylacetic acid useful as an intermediate for pharmaceutical products and the like, an intermediate therefor and a production method thereof.

BACKGROUND OF THE INVENTION

2-Cyclohexyl-2-hydroxy-2-phenylacetic acid and ester thereof are useful as intermediates for pharmaceutical products, such as oxybutynin, which is a therapeutic agent for pollakiuria, and the like. There have been proposed various production methods of 2-cyclohexyl-2-hydroxy-2-phenylacetic acid and ester thereof.

In J. Org. Chem., Vol. 42, No. 17, 2948–2949 (1977), 2-cyclohexyl-2-hydroxy-2-phenylacetic acid ester is obtained by reacting alkyl mandelate and lithium diisopropylamide, and then reacting the obtained reaction product with cyclohexyl iodide. According to this method, expensive lithium diisopropylamide is used in 2 equivalents or more relative to alkyl mandelate and expensive and unstable cyclohexyl iodide is used, which makes this method industrially disadvantageous.

According to JP-A-11-193271, ethyl benzoylformate and cyclohexylmagnesium bromide are condensed to give ethyl 2-cyclohexyl-2-hydroxy-2-phenylacetate, which is hydrolyzed to give 2-cyclohexyl-2-hydroxy-2-phenylacetic acid. In this condensation reaction, diethyl ether having a boiling point of 35° C. is used in an amount of about 12-fold volume relative to ethyl benzoylformate, manipulation of dangerous reaction using the boiling point of diethyl ether is required and the yield is as low as 53.3%. In an attempt to improve this method into an industrially safe one, the present inventors used tetrahydrofuran instead of diethyl ether as a solvent and reproduced the reaction. As a result, there occurred reduction due to Grignard reagent to produce ethyl mandelate as a by-product, as well as addition of the Grignard reagent to ester bond. The proportion of the starting material that became a by-product was 42% and the yield of the objective product was as low as 58%. After hydrolysis of the obtained crude ethyl 2-cyclohexyl-2-hydroxy-2-phenylacetate, it was subjected to recrystallization and the like to increase the purity but the yield from ethyl benzoylformate of 2-cyclohexyl-2-hydroxy-2-phenylacetic acid did not exceed 43%.

Therefore, it is concluded that none of the above methods produces 2-cyclohexyl-2-hydroxy-2-phenylacetic acid or ester thereof industrially, economically and safely in a good yield.

There have been also proposed various production methods of optically active 2-cyclohexyl-2-hydroxy-2-phenylacetic acid and ester thereof.

In WO00/23414, a method for optical resolution of a racemate of 2-cyclohexyl-2-hydroxy-2-phenylacetic acid using optically active amine is described. This method, nevertheless, is not entirely efficient because it produces undesirable enantiomer in a half amount.

In WO00/27786, moreover, (i) optically active mandelic acid is converted to 2-tert-butyl-5-phenyl-4-oxo-1,3-dioxolane protected by tert-butyl at the 2-position, by the use of pivalaldehyde, (ii) the resulting compound is reacted with cyclohexanone in the presence of lithium bis(trimethylsilyl)-amide at −78° C., and (iii) the reaction product is subjected to reduction and hydrolysis to give optically active 2-cyclohexyl-2-hydroxy-2-phenylacetic acid. This method is industrially disadvantageous in that lithium bis(trimethylsilyl)amide is expensive, the reaction needs to be carried out at an extremely low temperature of −78° C., a number of steps are required and the like.

In J. Med. Chem., 40, 117–124 (1997), moreover, as in WO00/27786, 2-tert-butyl-5-phenyl-4-oxo-1,3-dioxolane protected by tert-butyl at the 2-position is reacted with 3-cylcohexenyl bromide in the presence of lithium diisopropylamide at −80° C. and subjected to reduction and hydrolysis to give optically active 2-cyclohexyl-2-hydroxy-2-phenylacetic acid. This method is industrially disadvantageous in that lithium diisopropylamide and 3-cyclohexenyl bromide are expensive, the reaction needs to be carried out at an extremely low temperature of −80° C. and the like.

From the foregoing, it follows that none of the above methods produces optically active 2-cyclohexyl-2-hydroxy-2-phenylacetic acid and ester thereof industrially, economically and safely in a good yield.

SUMMARY OF THE INVENTION

It is therefore an object of the present invention to provide an industrial method of producing 2-cyclohexyl-2-hydroxy-2-phenylacetic acid, optically active form thereof and intermediates therefor, economically and safely in a good yield.

To solve the above-mentioned problems, the present inventors considered that novel 2-(2'-cyclohexen-1'-yl)-2-hydroxy-2-phenylacetic acid ester (compound of the formula [II] below) obtained by reacting cyclohexene and benzoylformic acid ester may be usable as a precursor of 2-cyclohexyl-2-hydroxy-2-phenylacetic acid and ester thereof, which are useful as intermediates for pharmaceutical products.

The reaction between cyclohexene and benzoylformic acid ester is called an ene reaction. In general, it is considered that a sterically complicated compound, such as benzoylformic acid ester, has poor reactivity and the reaction with olefin having a double bond in a ring, such as cyclohexene, is difficult to the degree that a reaction in a good yield is remotely available.

The present inventors have conducted this reaction in the presence of a Lewis acid, and surprisingly found that highly pure 2-(2'-cyclohexen-1'-yl)-2-hydroxy-2-phenylacetic acid ester could be obtained in a good yield. In addition, this reaction proceeds by an extremely simple manipulation of stirring at room temperature. It was found, therefore, that 2-cyclohexyl-2-hydroxy-2-phenylacetic acid and ester thereof could be obtained by a strategy completely different from conventional production, by the use of 2-(2'-cyclohexen-1'-yl)-2-hydroxy-2-phenylacetic acid ester as a precursor, which is subjected to reduction and hydrolysis.

It was also found that, while an environmentally necessarily preferable solvent, such as methylene chloride, is generally used for the ene reaction, incineratable monochlorobenzene can be used as an alternative solvent. Further, it was found that by converting benzoylformic acid to optically active benzoylformic acid ester having an asymmetric carbon atom in the ester moiety thereof (optically active form of compound of the formula [I] below) and then carrying out the aforementioned ene reaction, asymmetry is induced to give optically active 2-(2'-cyclohexen-1'-yl)-2-hydroxy-2-phenylacetic acid ester, and by subjecting this ester to hydrolysis and reduction, optically active 2-cyclohexyl-2-hydroxy-2-phenylacetic acid could be obtained.

Accordingly, the present invention provides (1) a compound of the formula [II]

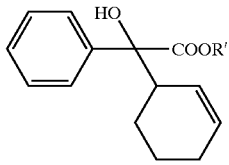

[II]

wherein R' is linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and (α-(2-cyclohexen-1-yl)-α-hydroxy-benzyl)carbonyloxy, or cyclohexyl, cyclopentyl or norbornyl, which is optionally substituted by at least one substituent selected from the group consisting of linear or branched chain alkyl having 1 to 15 carbon atom(s) and phenyl, or an optically active form thereof, (2) the compound of the above-mentioned (1) wherein R' is linear or branched chain alkyl having 1 to 15 carbon atom(s), which is optionally substituted by at least one substituent selected from the group consisting of phenyl, naphthyl, cyclohexyl, cyclopentyl and norbornyl, or cyclohexyl, cyclopentyl or norbornyl, which is optionally substituted by at least one substituent selected from the group consisting of linear or branched chain alkyl having 1 to 15 carbon atom(s) and phenyl, or an optically active form thereof, (3) a compound of the formula [V]

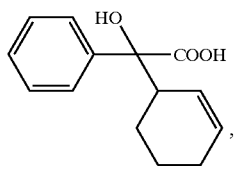

[V]

an optically active form thereof or a salt thereof, (4) a method for producing a compound of the formula [II]

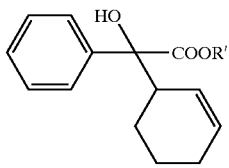

[II]

wherein R' is as defined in the above-mentioned (1), or an optically active form thereof, which method comprising reacting a compound the formula [I]

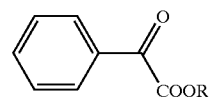

[I]

wherein R is linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and benzoylcarbonyloxy, or cyclohexyl, cyclopentyl or norbornyl, which is optionally substituted by at least one substituent selected from the group consisting of linear or branched chain alkyl having 1 to 15 carbon atom(s) and phenyl or an optically active form thereof, with cyclohexene in the presence of a Lewis acid, (5) the production method of the above-mentioned (4) wherein R and R' are each linear or branched chain alkyl having 1 to 15 carbon atom(s), which is optionally substituted by at least one substituent selected from the group consisting of phenyl, naphthyl, cyclohexyl, cyclopentyl and norbornyl, or cyclohexyl, cyclopentyl or norbornyl, which is optionally substituted by at least one substituent selected from the group consisting of linear or branched chain alkyl having 1 to 15 carbon atom(s) and phenyl, (6) the production method of the above-mentioned (4), wherein R and R' are each a group having an asymmetric carbon atom, (7) the production method of the above-mentioned (4), wherein the Lewis acid is an optically active Lewis acid having an asymmetric ligand, (8) the production method of the above-mentioned (4), wherein the Lewis acid is titanium tetrachloride, (9) the production method of any of the above-mentioned (4)–(8), wherein the reaction is carried out in monochlorobenzene,

(10) a method for producing a compound of the formula [III]

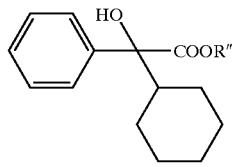

[III]

wherein R" is linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and (α-cyclohexyl-α-hydroxybenzyl)carbonyloxy, or cyclohexyl, cyclopentyl or norbornyl, which is optionally substituted by at least one substituent selected from the group consisting of linear or branched chain alkyl having 1 to 15 carbon atom(s) and phenyl or an optically active form, which method comprising reducing a compound of the formula [II]

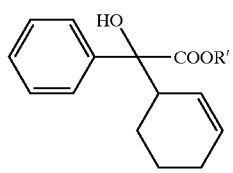

[II]

wherein R' is as defined in (1) above, or an optically active form thereof,

(11) the production method of the above-mentioned (10), wherein R' and R" are each linear or branched chain alkyl having 1 to 15 carbon atom(s), which is optionally substituted by at least one substituent selected from the group consisting of phenyl, naphthyl, cyclohexyl, cyclopentyl and norbornyl, or cyclohexyl, cyclopentyl or norbornyl, which is optionally substituted by at least one substituent selected from the group consisting of linear or branched chain alkyl having 1 to 15 carbon atom(s) and phenyl,

(12) a method for producing a compound of the formula [V]

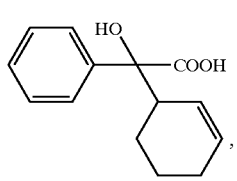

[V]

an optically active form thereof or a salt thereof, which method comprising hydrolyzing a compound of the formula [II]

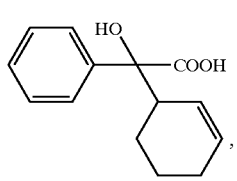

[II]

wherein R' is as defined in the above-mentioned (1), or an optically active form thereof,

(13) the production method of the above-mentioned (12), wherein R' is linear or branched chain alkyl having 1 to 15 carbon atom(s), which is optionally substituted by at least one substituent selected from the group consisting of phenyl, naphthyl, cyclohexyl, cyclopentyl and norbornyl, or cyclohexyl, cyclopentyl or norbornyl, which is optionally substituted by at least one substituent selected from the group consisting of linear or branched chain alkyl having 1 to 15 carbon atom(s) and phenyl,

(14) a method for producing 2-cyclohexyl-2-hydroxy-2-phenylacetic acid of the formula [IV]

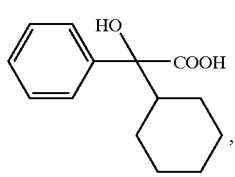

[IV]

an optically active form thereof or a salt thereof, which method comprising reducing a compound of the formula [V]

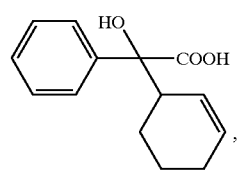

[V]

an optically active form thereof or a salt thereof,

(15) a method for producing 2-cyclohexyl-2-hydroxy-2-phenylacetic acid of the formula [IV]

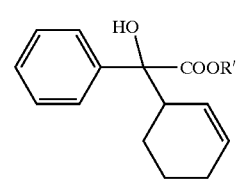

[IV]

an optically active form thereof or a salt thereof, which method comprising subjecting a compound of the formula [II]

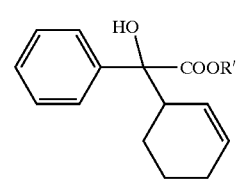

[II]

wherein R' is as defined in (1) above, or an optically active form thereof, to hydrolysis and reduction,

(16) the production method of the above-mentioned (15), wherein R' is linear or branched chain alkyl having 1 to 15 carbon atom(s), which is optionally substituted by at least one substituent selected from the group consisting of phenyl, naphthyl, cyclohexyl, cyclopentyl and norbornyl, or cyclohexyl, cyclopentyl or norbornyl, which is optionally substituted by at least one substituent selected from the group consisting of linear or branched chain alkyl having 1 to 15 carbon atom(s) and phenyl,

(17) the production method of the above-mentioned (15), which comprises simultaneous hydrolysis and reduction,

(18) the production method of the above-mentioned (15), which comprises hydrolysis after reduction,

(19) the production method of the above-mentioned (15), which comprises reduction after hydrolysis,

(20) a method for producing a compound of the formula [III]

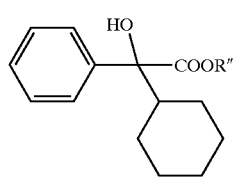

[III]

wherein R" is as defined in (10) above, or an optically active form thereof, which method comprising reacting a compound the formula [I]

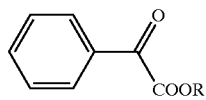

wherein R is as defined in (4) above, or an optically active form thereof, with cyclohexene in the presence of an Lewis acid to give a compound of the formula [II]

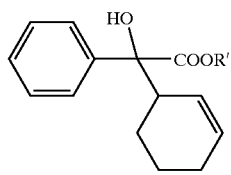

wherein R' is as defined in (1) above, or an optically active form thereof, and reducing the same,
(21) the production method of the above-mentioned (20) wherein R' and R" are each linear or branched chain alkyl having 1 to 15 carbon atom(s), which is optionally substituted by at least one substituent selected from the group consisting of phenyl, naphthyl, cyclohexyl, cyclopentyl and norbornyl, or cyclohexyl, cyclopentyl or norbornyl, which is optionally substituted by at least one substituent selected from the group consisting of linear or branched chain alkyl having 1 to 15 carbon atom(s) and phenyl,
(22) a method for producing a compound of the formula [V]

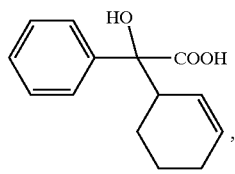

an optically active form thereof or a salt thereof, which method comprising reacting a compound of the formula [I]

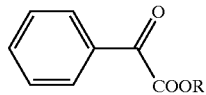

wherein R is as defined in (4) above, or an optically active form thereof, with cyclohexene in the presence of a Lewis acid to give a compound of the formula [II]

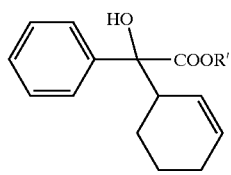

wherein R' is as defined in (1) above, or an optically active form thereof, and hydrolyzing the same,
(23) the production method of the above-mentioned (22), wherein R and R' are each linear or branched chain alkyl having 1 to 15 carbon atom(s), which is optionally substituted by at least one substituent selected from the group consisting of phenyl, naphthyl, cyclohexyl, cyclopentyl and norbornyl, or cyclohexyl, cyclopentyl or norbornyl, which is optionally substituted by at least one substituent selected from the group consisting of linear or branched chain alkyl having 1 to 15 carbon atom(s) and phenyl,
(24) a method of producing 2-cyclohexyl-2-hydroxy-2-phenylacetic acid of the formula [IV]

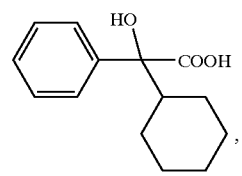

an optically active form thereof or a salt thereof, which method comprising reacting a compound of the formula [I]

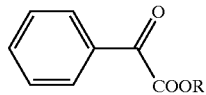

wherein R is as defined in (4) above, or an optically active form thereof, with cyclohexene in the presence of an Lewis acid to give a compound of the formula [II]

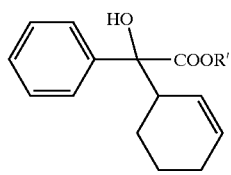

wherein R' is as defined in (1) above, or an optically active form thereof, and subjecting the same to hydrolysis and reduction,
(25) the production method of the above-mentioned (24), wherein R and R' are each linear or branched chain alkyl having 1 to 15 carbon atom(s), which is optionally substituted by at least one substituent selected from the group consisting of phenyl, naphthyl, cyclohexyl, cyclopentyl and norbornyl, or cyclohexyl, cyclopentyl or norbornyl, which is optionally substituted by at least one substituent selected from the group consisting of linear or branched chain alkyl having 1 to 15 carbon atom(s) and phenyl,
(26) the production method of the above-mentioned (24), which comprises simultaneous hydrolysis and reduction,
(27) the production method of the above-mentioned (24), which comprises hydrolysis after reduction, and
(28) the production method of the above-mentioned (24), which comprises reduction after hydrolysis.

DETAILED DESCRIPTION OF THE INVENTION

The present invention is explained in detail in the following.

Each symbol used in this specification is defined in the following.

The alkyl in the present invention is linear as long as it does not have a prefix (e.g., iso, neo, sec-, tert-etc.). For example, a simple propyl means linear propyl.

The "linear or branched chain alkyl having 1 to 15 carbon atom(s)" of the "linear or branched chain alkyl having 1 to 15 carbon atom(s), which is optionally substituted by at least one substituent selected from the group consisting of phenyl, naphthyl, cyclohexyl, cyclopentyl and norbornyl" is exemplified by methyl, ethyl, propyl, isopropyl, butyl, isobutyl, sec-butyl, tert-butyl, pentyl, isopentyl, neopentyl, hexyl, heptyl, decyl, pentadecyl and the like, with preference given to alkyl having 1 to 6 carbon atoms, which is more preferably methyl, ethyl, isopropyl and butyl.

The "linear or branched chain alkyl having 1 to 15 carbon atom(s), which is optionally substituted by at least one substituent selected from the group consisting of phenyl, naphthyl, cyclohexyl, cyclopentyl and norbornyl" is exemplified by methyl, ethyl, isopropyl, butyl, 1-phenylethyl, 2-phenylethyl, 1-naphthylethyl, 2-naphthylethyl, cyclohexylmethyl, cyclopentylmethyl, 2-norbornylmethyl, 2-methylbutyl, 1-methylpropyl, 1-methylbutyl, 1-methylpentyl, 1-methylhexyl, 1-methylheptyl, 1-methyloctyl, 1-methylnonyl, 1-methyldecyl and the like, with preference given to methyl, ethyl, isopropyl, butyl and 2-phenylethyl.

The "linear or branched chain alkyl having 1 to 15 carbon atom(s)" in the "linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and benzoylcarbonyloxy", "linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and ($\alpha$-(2-cyclohexen-1-yl)-$\alpha$-hydroxybenzyl)-carbonyloxy" and "linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and ($\alpha$-cyclohexyl-$\alpha$-hydroxybenzyl)carbonyloxy" is as defined for the above-mentioned "linear or branched chain alkyl having 1 to 15 carbon atom(s)".

Examples of the "linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and benzoylcarbonyloxy" include examples recited for the above-mentioned "linear or branched chain alkyl having 1 to 15 carbon atom(s), which is optionally substituted by at least one substituent selected from the group consisting of phenyl, naphthyl, cyclohexyl, cyclopentyl and norbornyl", 1-(methoxycarbonyl)ethyl, 1,2-bis(ethoxycarbonyl)-2-(benzoylcarbonyloxy)ethyl and the like. Of these, methyl, ethyl, isopropyl, butyl, 2-phenylethyl, 1-(methoxycarbonyl)ethyl and 1,2-bis(ethoxycarbonyl)-2-(benzoylcarbonyloxy) ethyl are preferable.

Examples of the "linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and ($\alpha$-(2-cyclohexen-1-yl)-$\alpha$-hydroxybenzyl)carbonyloxy" include examples recited for the above-mentioned "linear or branched chain alkyl having 1 to 15 carbon atom(s), which is optionally substituted by at least one substituent selected from the group consisting of phenyl, naphthyl, cyclohexyl, cyclopentyl and norbornyl", 1-(methoxycarbonyl)ethyl, 1,2-bis (ethoxycarbonyl)-2-(($\alpha$-(2-cyclohexen-1-yl)-$\alpha$-hydroxybenzyl)carbonyloxy)ethyl and the like. Of these, methyl, ethyl, isopropyl, butyl, 2-phenylethyl, 1-(methoxycarbonyl)ethyl and 1,2-bis(ethoxycarbonyl)-2-(($\alpha$-(2-cyclohexen-1-yl)-$\alpha$-hydroxybenzyl)carbonyloxy) ethyl are preferable.

Examples of the "linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and ($\alpha$-cyclohexyl-$\alpha$-hydroxybenzyl)carbonyloxy" include examples recited for the above-mentioned "linear or branched chain alkyl having 1 to 15 carbon atom(s), which is optionally substituted by at least one substituent selected from the group consisting of phenyl, naphthyl, cyclohexyl, cyclopentyl and norbornyl", 1-(methoxycarbonyl)ethyl, 1,2-bis(ethoxycarbonyl)-2-(($\alpha$-cyclohexyl-$\alpha$-hydroxybenzyl)carbonyloxy)ethyl and the like. Of these, methyl, ethyl, isopropyl, butyl, 2-phenylethyl, 1-(methoxycarbonyl)ethyl and 1,2-bis(ethoxycarbonyl)-2-(($\alpha$-cyclohexyl-$\alpha$-hydroxybenzyl)carbonyloxy)ethyl are preferable.

The "linear or branched chain alkyl having 1 to 15 carbon atom(s)" of the "cyclohexyl, cyclopentyl or norbornyl, which is optionally substituted by at least one substituent selected from the group consisting of linear or branched chain alkyl having 1 to 15 carbon atom(s) and phenyl" is as defined for the above-mentioned "linear or branched chain alkyl having 1 to 15 carbon atom(s)".

Examples of the "cyclohexyl, cyclopentyl or norbornyl, which is optionally substituted by at least one substituent selected from the group consisting of linear or branched chain alkyl having 1 to 15 carbon atom(s) and phenyl" include cyclohexyl, 2-methylcyclohexyl, 4-methylcyclohexyl, 4-t-butylcyclohexyl, cyclopentyl, 2-methylcyclopentyl, 2-norbornyl, isobornyl, bornyl, menthyl, isomenthyl, neomenthyl, 8-phenylmenthyl and the like, with preference given to cyclohexyl, 2-methylcyclohexyl and cyclopentyl.

In view of the availability of the starting material compound (compound [I]) and the reaction speed in each step, R is particularly preferably methyl or ethyl.

As R, one having an asymmetric carbon atom can be also used, such as menthyl, isomenthyl, neomenthyl, bornyl, 8-phenylmenthyl and norbornyl having an asymmetric carbon atom; 1-phenylethyl, 1-naphthylethyl, 2-methylcyclohexyl, 2-methylbutyl, 1-methylethyl, 1-methylpropyl, 1-methylbutyl, 1-methylpentyl, 1-methylhexyl, 1-methylheptyl, 1-methyloctyl, 1-methylnonyl, 1-methyldecyl, 1-(methoxycarbonyl)ethyl and 1,2-bis(ethoxycarbonyl)-2-(benzoylcarbonyloxy)ethyl, which are R-compounds and S-compounds; and the like.

As R', one having an asymmetric carbon atom can be also used, such as menthyl, isomenthyl, neomenthyl, bornyl, 8-phenylmenthyl and norbornyl having an asymmetric carbon atom; 1-phenylethyl, 1-naphthylethyl, 2-methylcyclohexyl, 2-methylbutyl, 1-methylethyl, 1-methylpropyl, 1-methylbutyl, 1-methylpentyl, 1-methylhexyl, 1-methylheptyl, 1-methyloctyl, 1-methylnonyl, 1-methyldecyl, 1-(methoxycarbonyl)ethyl and 1,2-bis(ethoxycarbonyl)-2-(($\alpha$-(2-cyclohexen-1-yl)-$\alpha$-hydroxy-benzyl)carbonyloxy)ethyl, which are R-compounds and S-compounds; and the like.

As R", one having an asymmetric carbon atom can be also used, such as menthyl, isomenthyl, neomenthyl, bornyl, 8-phenylmenthyl and norbornyl having an asymmetric carbon atom; 1-phenylethyl, 1-naphthylethyl, 2-methylcyclohexyl, 2-methylbutyl, 1-methylethyl, 1-methylpropyl, 1-methylbutyl, 1-methylpentyl, 1-methylhexyl, 1-methylheptyl, 1-methyloctyl, 1-methylnonyl, 1-methyldecyl, 1-(methoxycarbonyl)ethyl, 1,2-bis(ethoxycarbonyl)-2-(($\alpha$-cyclohexyl-$\alpha$- hydroxybenzyl)-carbonyloxy)ethyl, which are R-compounds and S-compounds; and the like.

In the present invention, the compound [II]-compound [V] have an asymmetric carbon atom, wherein, for example, compound [II]-compound [V] have an asymmetric carbon atom at the 2-position of the acetic acid skeleton, compound [II] and compound [V] have an asymmetric carbon atom at the binding site of cyclohexene, and compound [I], compound [II] and compound [III] may have one or more asymmetric carbon atoms at substituent R. The compound [I]-compound [V] of the present invention encompass any imaginable optically active forms and mixtures thereof (e.g., racemate, enantiomer mixture, diastereomer mixture and the like).

The compound [IV] and compound [V] have a carboxyl group and may be in the form of a salt. Examples of the salts of compound [IV] and compound [V] include salts with alkali metal (e.g., sodium, potassium, lithium etc.), amines (e.g., ammonia, methylamine, dimethylamine, triethylamine etc.) and the like.

The production method of the present invention is shown in the following reaction scheme.

added, or cyclohexene and a Lewis acid are added to a solvent and then compound [I] may be added.

The Lewis acid to be used in 1) may be, for example, titanium tetrachloride, titanium tetrabromide, tin tetrachloride, silicon tetrachloride, zirconium tetrachloride, aluminum chloride, dimethylaluminum chloride, methylaluminum dichloride, aluminum bromide, ferric chloride, zinc chloride, zinc bromide, zinc iodide, zinc trifluoromethanesulfonate, magnesium chloride, magnesium bromide, magnesium iodide, magnesium trifluoromethanesulfonate, boron trifluoride, hafnium trifluoromethanesulfonate, lanthanum trifluoromethanesulfonate, scandium trifluoromethanesulfonate, ytterbium trifluoromethanesulfonate and the like, preferably titanium tetrachloride. An optically active Lewis acid having an asymmetric ligand may be used for obtaining an optically active form. Examples of the asymmetric ligand include R- or S-1,1'-bi-2-naphthol and the like.

The amount of use of the Lewis acid is generally 0.005 mol–5 mol, preferably 0.1 mol–2 mol, more preferably 1 mol–1.5 mol, per 1 mol of compound [I].

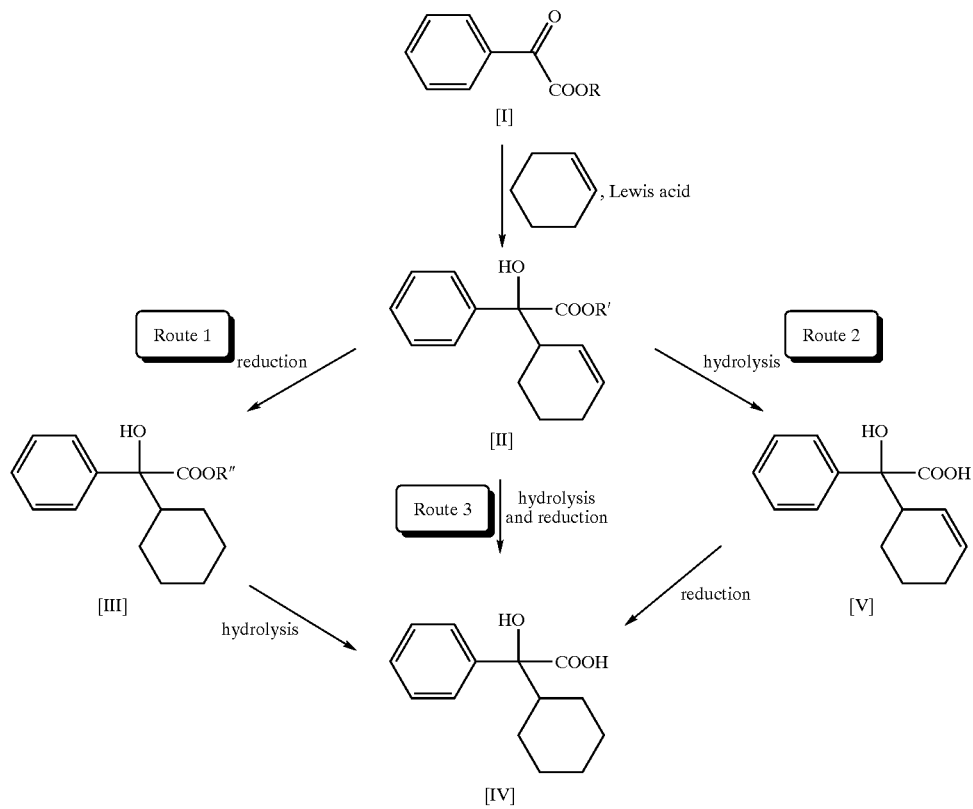

wherein each symbol is as defined above.

1) Production Method of Compound [II]

The compound [II] is a novel compound, which can be obtained by, for example, reacting compound [I] with cyclohexene in a solvent in the presence of a Lewis acid. The order of addition of reagents is not particularly limited. For example, compound [I] and cyclohexene are added to a solvent and then a Lewis acid may be added, or compound [I] and a Lewis acid are added to a solvent and then cyclohexene may be added, or a Lewis acid is added to a solvent and then compound [I] and cyclohexene may be The amount of cyclohexene used in 1) is generally 0.8 mol–5 mol, preferably 1 mol–3 mol, more preferably 1.2 mol–2.2 mol, per 1 mol of compound [I].

Examples of the solvent to be used in 1) include methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, monofluorobenzene, nitrobenzene, carbon disulfide, toluene, acetonitrile, propionitrile, nitromethane, nitroethane, water, methanol, ethanol and the like, with preference given to methylene chloride, 1,2-dichloroethane, monochlorobenzene, 1,2-dichlorobenzene, 2-chlorotoluene, 3-chlorotoluene and 4-chlorotoluene. In view of the yield and incineratability of compound [II], monochlorobenzene, 2-chlorotoluene, 4-chlorotoluene and nitrobenzene are more preferable, which is most preferably monochlorobenzene.

The amount of use of the solvent is generally 1 L–50 L, preferably 3 L–30 L, more preferably 5 L–20 L, per 1 kg of compound [I].

While the reaction conditions in 1) depend on the reagent to be used and the like, the reaction is generally carried out at −30° C. to 150° C., preferably 0° C. to 80° C., more preferably 15° C. to 60° C., generally for 1 h–24 h, preferably 3 h–15 h.

The compound [II] can be separated and purified by conventional methods. For example, a reaction mixture is poured into water, and after partitioning, an organic layer is washed and filtrated, and the obtained filtrate is washed, dried and concentrated under reduced pressure to separate compound [II]. After separation, silica gel column chromatography may be applied for purification. When compound [II] is obtained in the form of a mixture of an optically active form, it can be resolved into each optically active form by conventional methods such as optical resolution and the like.

The compound [I], which is a starting material in 1), may be commercially available. Alternatively, one obtained by transesterification of methyl benzoylformate and a compound of ROH (R is as defined above), by esterification of benzoylformic acid and a compound of ROH (R is as defined above), or by reaction of a reactive derivative of benzoylformic acid and a compound of ROH (R is as defined above) can be used. An optically active compound [I] wherein R has an asymmetric carbon atom can be obtained using optically active ROH wherein R has an asymmetric carbon atom (e.g., compound such as lactic acid ester (e.g., methyl lactate etc.) and tartaric acid ester (e.g., diethyl tartrate etc.) and the like). When an optically active compound [I] wherein R has an asymmetric carbon atom is used as the starting material for the "production method of compound [II]", the carbon atom at the 2-position of the acetic acid skeleton induces chirality to produce an optically active compound [II].

2) Production Method of Compound [IV]

The compound [IV] can be produced by subjecting compound [II] to hydrolysis and reduction. The order of hydrolysis and reduction is not particularly limited. For example, Route 1: hydrolysis after reduction of compound [II],
Route 2: reduction after hydrolysis of compound [II], or
Route 3: simultaneous hydrolysis and reduction of compound [II] is employed to give compound [IV]. The compound [II], which is a starting material used for Routes 1–3, can be produced according to the method of the above-mentioned 1). In the following, each Route is explained in detail.

2-1) Route 1

In Route 1, compound [II] is reduced to give compound [III], which is hydrolyzed to give compound [IV]. The production method of compound [III], namely, reduction of compound [II] is described in detail.

2-1-1) Production Method of Compound [III]

The compound [III] can be obtained by reduction of compound [II]. The reduction can be conducted according to a conventional method. For example, compound [II] is reacted with hydrogen in a solvent in the presence of a reduction catalyst. It is also possible to add active charcoal simultaneously with the reduction catalyst. When an optically active compound [II] is used as a starting material, optically active compound [III] retaining the steric configuration of the carbon atom at the 2-position of the acetic acid skeleton of the starting material can be obtained.

Examples of the reduction catalyst to be used in 2-1-1) include palladium carbon, palladium, palladium hydroxide, platinum oxide, platinum, platinum carbon, ruthenium oxide, ruthenium, ruthenium carbon and the like, with preference given to palladium carbon and platinum oxide, and more preference given to palladium carbon. The amount of use of the reduction catalyst is generally 0.00001 mol–0.2 mol, preferably 0.0001 mol–0.1 mol, per 1 mol of compound [II].

Examples of the solvent to be used in 2-1-1) include water, methanol, ethanol, isopropyl alcohol, acetic acid, ethyl acetate and the like, and mixed solvents thereof, with preference given to water, methanol, ethanol, a mixed solvent of methanol and water and a mixed solvent of ethanol and water. The residual solvent, by-product and the like from the production process of compound [II], which is the starting material, may cause production of a slight amount of an acid due to the simultaneous reduction during reduction of compound [II]. In such a case, an appropriate amount of a base (e.g., triethylamine, sodium acetate and the like) to neutralize the acid produced during this reduction step is preferably added.

The amount of use of the solvent is generally 0.1 L–20 L, preferably 0.5 L–8 L, more preferably 1 L–6 L, relative to 1 kg of compound [II].

The amount of use of hydrogen in 2-1-1) is not particularly limited as long as it can reduce compound [II].

While the reaction conditions in 2-1-1) depend on the kind and the amount of the reduction catalyst, the starting material to be used and the like, the reaction is carried out at generally −20° C. to 150° C., preferably 0° C. to 100° C., more preferably 15° C. to 60° C., generally for 1 h–24 h, preferably 3 h–15 h.

The reaction pressure in 2-1-1) is generally 101 kPa–3040 kPa, preferably 101 kPa–2020 kPa, more preferably 202 kPa–1530 kPa.

The compound [III] may be subjected to hydrolysis without separation or purification. For separation and purification, conventional methods can be used. When compound [III] is obtained as a mixture of an optically active form, it can be resolved into each optically active form according to a conventional method such as optical resolution and the like.

2-1-2) Hydrolysis of Compound [III]

The hydrolysis of compound [III] is now described in detail.

The hydrolysis of compound [III] is conducted according to a conventional method. For example, by (a) reaction of compound [III] and alkali metal compound in a solvent, followed by neutralization with an acid, where necessary, or by (b) reaction of compound [III] with an inorganic acid in a solvent, compound [IV] or a salt thereof can be obtained. When an optically active compound [III] is used as a starting material, optically active compound [IV] retaining the steric configuration of the starting material can be obtained.

As the solvent to be used in (a) and (b), there are mentioned, for example, methanol, ethanol, water and the like and mixed solvents thereof, with preference given to a mixed solvent of methanol and water and a mixed solvent of ethanol and water. As the solvent, the solvent used for reduction of compound [II] can be used as it is for this hydrolysis. When the solvent used for reduction of compound [II] is utilized, evaporation of the solvent after production of compound [III] is not necessary, which is economical and shortens the step. The amount of use of this solvent is generally 1 L–50 L, preferably 5 L–20 L, in the case of (a), and generally 1 L–30 L, preferably 5 L–15 L, in the case of (b), per 1 kg of compound [III] (per 1 kg of compound [II] when subjected to hydrolysis without separation of compound [III] after reduction of compound [II]).

As the alkali metal compound to be used in (a), for example, sodium hydroxide and potassium hydroxide are mentioned, with preference given to sodium hydroxide. The amount of use of this alkali metal compound is generally 1 mol–3.3 mol, preferably 1 mol–2.2 mol, per 1 mol of compound [III] (per 1 mol of compound [II] when subjected to hydrolysis without separation of compound [III] after reduction of compound [II]). While the amount varies depending on the kind of alkali metal compound and solvent, alkali metal compound is used in an amount to make the concentration in the reaction system generally 0.1 wt %–50 wt %, preferably 3 wt %–25 wt %. The alkali metal compound may be added to the reaction system as it is, but addition in the form of an aqueous solution or alcohol solution is preferable. The amount of use of the solvent to dissolve the alkali metal compound is included in the amount of use of the above-mentioned solvent.

Examples of the inorganic acid to be used in (b) include hydrochloric acid, sulfuric acid, phosphoric acid and the like, with preference given to hydrochloric acid and sulfuric acid. The amount of use of the inorganic acid is generally 0.01 mol–5 mol, preferably 0.1 mol–2 mol, per 1 mol of compound [III] (per 1 mol of compound [II] when subjected to hydrolysis without separation of compound [III] after reduction of compound [II]).

The acid to be used for neutralization in (a) is exemplified by those mentioned with regard to the "inorganic acid to be used in (b)" above. The acid is used in an amount that makes the pH of the reaction mixture generally not more than 7, preferably not more than 4. When neutralization with acid is not performed in (a), an alkali metal salt of compound [IV] is obtained and when the starting material (compound [III]) is in an optically active form, an alkali metal salt of optically active compound [IV] is obtained.

In (a), while the conditions of the reaction between compound [III] and alkali metal compound depend on the kind and the amount of use of compound [III] and alkali metal compound, and the like, the reaction completes generally at a temperature of not less than 0° C., preferably not less than 60° C., and generally not higher than 180° C., preferably not higher than 150° C., more preferably not higher than 120° C., and most preferably not higher than 100° C., generally for not less than lo 30 min, preferably not less than 2 h; and generally within 15 h, preferably within 8 h, more preferably within 6 h.

The reaction conditions in (b) depend on the kind and the amount of use of compound [III] and inorganic acid to be used, and the like, but the reaction generally ends at 0° C.–120° C., preferably 60° C.–100° C., generally for 1 h–24 h, preferably 4 h–10 h.

2-2) Route 2

In Route 2, compound [II] is hydrolyzed to give novel compound [V], which is reduced to give compound [IV]. First, the production method of compound [V], namely, hydrolysis of compound [II] is described in detail.

2-2-1) Production Method of Compound [V]

The compound [V] is a novel compound and can be obtained by hydrolysis of compound [II]. The compound [II] can be hydrolyzed according to completely the same method as in the above-mentioned "2-1-2) Hydrolysis of compound [III]", and the alkali metal compound, inorganic acid and solvent to be used are the same. The amounts of alkali metal compound, inorganic acid and solvent to be used in 2-2-1) are those obtained by changing the standard from compound [III] to compound [II].

However, when compound [II] is hydrolyzed according to the method of (a) in the above-mentioned "2-1-2) Hydrolysis of compound [III]", neutralization with an acid after hydrolysis is not necessarily essential, and compound [V] can be subjected to reduction as it is.

When an optically active compound [II] is used as a starting material, optically active compound [V] retaining the steric configuration of the starting material can be obtained. It is needless to say that the method of (a) without neutralization after hydrolysis of compound [II] affords an alkali metal salt of optically active compound [V].

The compound [V] can be separated and purified by a conventional method. For example, the crystals obtained by reaction are aged where necessary, and subjected to filtration, washing and drying to separate and purify compound [V]. The compound [V] can be also used for the next step without separation. When compound [V] is obtained in the form of a mixture of an optically active form, it can be resolved into each optically active form by conventional methods such as optical resolution and the like.

2-2-2) Reduction of Compound [V]

The compound [V] can be reduced according to the method completely the same as the method of the above-mentioned "2-1-1) Production method of compound [III]", and the reduction catalyst and solvent to be used are the same. The amounts of reduction catalyst and solvent to be used in 2-2-2) are those obtained by changing the standard from compound [II] to compound [V]. When the compound [V] is reduced without separation after hydrolysis of compound [II], the standard is compound [II]. As in Route 1, the use of the same solvent for hydrolysis and reduction in Route 2 is preferable from the aspect of the number of steps and economical production.

When an optically active compound [V] is used as a starting material, optically active compound [IV] retaining the steric configuration of the carbon atom at the 2-position of the acetic acid skeleton of the starting material can be obtained.

2-3) Route 3

In Route 3, since hydrolysis and reduction of compound [II] simultaneously proceed, the reaction system is considered to contain compound [III] and compound [V] as intermediates. According to Route 3, the reagents necessary for reduction and hydrolysis and compound [II] are simultaneously added to the solvent and reacted to give compound [IV]. When an optically active compound [II] is used as a starting material, optically active compound [IV] retaining the steric configuration of the carbon atom at the 2-position of the acetic acid skeleton of the starting material can be obtained.

The solvent to be used in Route 3 may be the solvent used for "2-1-2) Hydrolysis of compound [III]", and the amount of use of the solvent is the same as that in the case of "2-1-2) Hydrolysis of compound [III]" (standard being not compound [III] but compound [II]).

The reduction in Route 3 can be carried out using a reduction catalyst and hydrogen in the same manner as in "2-1-1) Production method of compound [III]". The reduction catalyst is similar to that used for "2-1-1) Production method of compound [III]". The amounts of use of hydrogen and reduction reagent in Route 3 are the same as those in the case of "2-1-1) Production method of compound [III]".

The hydrolysis in Route 3 can be carried out according to two methods using (A) alkali metal compound (where necessary, an acid) or (B) inorganic acid, as in the "2-1-2) Hydrolysis of compound [III]". Each reagent may be that used for the "2-1-2) Hydrolysis of compound [III]" and the amount of use of each reagent is the same as that in the "2-1-2) Hydrolysis of compound [III]" (standard being not compound [III] but compound [II]).

The Route 3 proceeds at a reaction pressure of generally 101 kPa–3040 kPa, preferably 101 kPa–2020 kPa, more preferably 202 kPa–1530 kPa, at generally 0–150° C., preferably 50–100° C., for generally 1 h–24 h, preferably 5 h–15 h.

The compound [IV] obtained in Routes 1–3 can be separated and purified by conventional methods. For example, a reaction mixture is partitioned, the obtained organic layer is cooled to allow precipitation of crystals, and the crystals are aged, filtered, washed and dried for separation and purification. It is also possible to add an organic solvent, where necessary, before partitioning. For efficient removal of by-produced mandelic acid, benzoylformic acid and the like, the reaction mixture is preferably washed with a base, such as ammonia and the like, before partitioning (when organic solvent is added before partitioning, after the addition)) to make the pH of the washing 4–7 (preferably 4.5–6).

When compound [IV] or a salt thereof obtained by Routes 1–3 is a mixture of an optically active form, it can be resolved into each optically active form by conventional methods such as optical resolution and the like.

The compound [IV] can be introduced into oxybutynin useful as a therapeutic agent for pollakiuria, according to the method described in, for example, WO00/23414.

EXAMPLES

The present invention is explained in detail by referring to examples. The present invention is not limited by these examples in any way.

Example 1

Methyl 2-(2'-cyclohexen-1'-yl)-2-hydroxy-2-phenylacetate (Compound [II])

Methyl benzoylformate (41.0 g, 0.25 mol) and cyclohexene (41.0 g, 0.50 mol) were dissolved in methylene chloride (287 ml) under a nitrogen atmosphere, and titanium tetrachloride (60.7 g, 0.32 mol) was added dropwise thereto at 15–25° C. over 30 min, which was followed by stirring at 25–30° C. for 5 h. The reaction mixture was poured into water (287 ml) and partitioned. The organic layer was washed with 10 wt % aqueous sodium carbonate solution (287 g) and filtrated. The organic layer was washed with water (287 ml) again and dried over anhydrous magnesium sulfate (10 g). The organic layer is concentrated under reduced pressure to give a crude product (62.6 g) of the title compound. The crude product is purified by silica gel column chromatography to give the title compound (44.9 g, yield: 72.9%) as a diastereomer mixture of (2S*,1'S*) compound and (2S*,1'R*) compound.

$^1$H-NMR(400 MHz, CDCl$_3$) δ=1.24–1.77 (4H, m), 1.92–2.06 (2H, m) 3.14–3.21 (1H, m), 3.44 (1H, s), 3.80 (0.45H, s), 3.81 (2.55H, s), 5.13–5.18 (0.15H, m), 5.40–5.45 (0.85H, m), 5.75–5.80 (0.15H, m), 5.92–5.98 (0.85H, m), 7.26–7.32 (1H, m), 7.33–7.39 (2H, m), 7.62–7.69 (2H, m) ppm Example 2

2-(2'-Cyclohexen-1'-yl)-2-hydroxy-2-phenylacetic acid (Compound [V])

A diastereomer mixture (44.0 g) of (2S*,1'S*) compound and (2S*,1'R*) compound of methyl 2-(2'-cyclohexen-1'-yl)-2-hydroxy-2-phenylacetate reacted and purified by the same method as in Example 1 was dissolved in methanol (440 ml) and 48.5 wt % aqueous sodium hydroxide solution (30.1 g) was added. The mixture was stirred at 65–70° C. for 1 h. After confirmation of disappearance of ester compound (methyl 2-(2'-cyclohexen-1'-yl)-2-hydroxy-2-phenylacetate) by HPLC, methanol was evaporated under reduced pressure. The pH was adjusted to 1 with 6N hydrochloric acid and the resulted crystals were filtered, washed with water and dried under reduced pressure to give the title compound (40.5 g, yield :97.5%) as a diastereomer mixture of (2S*,1'S*) compound and (2S*,1'R*) compound.

$^1$H-NMR(400 MHz, CDCl$_3$) δ=1.18–1.76 (4H, m), 1.84–1.91 (0.3H, m) 1.93–2.07 (1.7H, m), 3.00–3.40 (1H, br), 3.23–3.37 (1H, m), 5.11–5.16 (0.15H, m), 5.52–5.57 (0.85H, m), 5.85–5.91 (0.15H, m), 6.04–6.11 (0.85H, m), 7.28–7.40 (3H, m), 7.64–7.70 (2H, m) ppm Example 3

2-(2'-Cyclohexen-1'-yl)-2-hydroxy-2-phenylacetic acid (Compound [V])

Crude methyl 2-(2'-cyclohexen-1'-yl)-2-hydroxy-2-phenylacetate (62.0 g) obtained on a similar scale to and by the method of Example 1 was dissolved in methanol (410 ml) and 48.5 wt % aqueous sodium hydroxide solution (41.2 g) was added. The mixture was stirred at 65–70° C. for 1 h. After confirmation of disappearance of ester compound (methyl 2-(2'-cyclohexen-1'-yl)-2-hydroxy-2-phenylacetate) by HPLC, methanol was evaporated at 65–85° C. under reduced pressure. Toluene (300 ml) and water (100 ml) were inpoured, and the aqueous layer was adjusted to pH 1 or below at 60–70° C. with 6N hydrochloric acid. The mixture was partitioned by allowing to stand at 60–70° C. and the organic layer was cooled to 0–5° C. The precipitated crystals were aged for 1 h at the same temperature, filtered, washed with cooled toluene (50 ml) and dried under reduced pressure at 65–75° C. to give the title compound as a diastereomer mixture (34.0 g) of (2S*,1'S*) compound and (2S*, 1'R*) compound.

yield from methyl benzoylformate: 58.5% purity: 98.8%.

$^1$H-NMR(400 MHz, CDCl$_3$) δ=1.18–1.76 (4H, m), 1.84–1.91 (0.2H, m), 1.93–2.07 (1.8H, m), 3.00–3.40 (1H, br), 3.23–3.37 (1H, m), 5.11–5.16 (0.1H, m), 5.52–5.57 (0.9H, m), 5.85–5.91 (0.1H, m), 6.04–6.11 (0.9H, m), 7.28–7.40 (3H, m), 7.64–7.70 (2H, m) ppm Example 4

2-Cyclohexyl-2-hydroxy-2-phenylacetic acid (Compound [IV], Route 1)

Crude methyl 2-(2'-cyclohexen-1'-yl)-2-hydroxy-2-phenylacetate (62.6 g) obtained on a similar scale to and by the method of Example 1 was dissolved in methanol (287 ml) and 5% palladium carbon (Kawaken Fine Chemicals Co., Ltd., type M, 0.82 g) was added. The mixture was stirred in a hydrogen gas (350 kPa) for 8 h and the catalyst was filtered off. A 48.5 wt % aqueous sodium hydroxide solution (41.5 g) was added and the mixture was stirred at 75–80° C. for 4 h. After confirmation of disappearance of ester compound (methyl 2-cyclohexyl-2-hydroxy-2-phenylacetate) by HPLC, methanol was evaporated under reduced pressure at 65–85° C. Toluene (164 ml) was inpoured, and the aqueous layer was adjusted to pH 1 or below with 6N hydrochloric acid at 60–70° C. The mixture was partitioned by allowing to stand at 60–70° C. and the organic layer was cooled to 0–5° C. The organic layer was aged for 1 h at the same temperature, filtrated, washed with cooled toluene (50 ml) and dried under reduced pressure at 65–75° C. to give the title compound (36.9 g).

yield from methyl benzoylformate: 63.1% purity: 99.3%.

$^1$H-NMR(400 MHz, CDCl$_3$) δ=0.99–1.48 (6H, m), 1.58–1.68 (3H, m), 1.78–1.83 (1H, m), 2.22–2.30 (1H, m), 3.25–3.60 (1H, br), 7.26–7.37 (3H, m), 7.63–7.66 (2H, m) ppm

Example 5

2-Cyclohexyl-2-hydroxy-2-phenylacetic acid (Compound [IV], Route 2)

Crude methyl 2-(2'-cyclohexen-1'-yl)-2-hydroxy-2-phenylacetate (64.1 g) obtained on a similar scale to and by the method of Example 1 was dissolved in methanol (287 ml) and 48.5 wt % aqueous sodium hydroxide solution (41.5 g) was added. The mixture was stirred at 75–80° C. for 4 h. After confirmation of disappearance of ester compound (methyl 2-(2'-cyclohexen-1'-yl)-2-hydroxy-2-phenylacetate) by HPLC, the aqueous layer was neutralized with 6N hydrochloric acid to pH 7. The resulting salt was filtrated, and 5% palladium carbon (Kawaken Fine Chemicals Co., Ltd., type M, 0.82 g) was added. The mixture was stirred in a hydrogen gas (350 kPa) for 8 h. The catalyst was filtered off and the residue was adjusted to pH 1 with 6N hydrochloric acid. Methanol was evaporated under reduced pressure and toluene (164 ml) was added. The mixture was partitioned by allowing to stand at 60–70° C. and the organic layer was cooled to 0–5° C. The organic layer was aged at the same temperature for 1 h, filtrated, washed with cooled toluene (50 ml) and dried under reduced pressure at 65–75° C. to give the title compound (36.4 g).

yield from methyl benzoylformate: 62.2%, purity: 99.0%,

The $^1$H-NMR spectrum data were the same as those obtained in Example 4.

Comparative Example 1

Synthesis of 2-cyclohexyl-2-hydroxy-2-phenylacetic acid by Grignard Method

Magnesium (15.8 g) and iodine (200 mg) were added to tetrahydrofuran (73 g) under a nitrogen atmosphere and the mixture was stirred at about 25° C. for 30 min. Cyclohexyl bromide (4.1 g) was added dropwise, tetrahydrofuran (291.9 g) was added and cyclohexyl chloride (86 g) was added dropwise at 60–70° C. The mixture was stirred at 60–75° C. for 2 h and analyzed by gas chromatography. As a result, the remainder of cyclohexyl chloride was 0.1%. The mixture was cooled to 20–30° C. and Grignard solution was added dropwise to a mixture of methyl benzoylformate (82.1 g) and tetrahydrofran (82 ml) at 6–14° C. The dropwise addition ended in 1 h. The mixture was stirred at the same temperature for 1 h and analyzed by HPLC. As a result, methyl benzoylformate was not detected. Tetrahydrofran was evaporated under reduced pressure at 65–80° C. The evaporated amount was 345 ml. Toluene (164 ml) was added and the mixture was added dropwise at 5–38° C. to 7N hydrochloric acid (215 ml) and partitioned by allowing to stand. The pure yield of methyl 2-cyclohexyl-2-hydroxy-2-phenylacetate in the organic layer was calculated by HPLC external standard method using a reference standard. As a result, yield was 58% (42% was by-product other than the objective product).

Methanol (82 ml) was added to the organic layer and 27 wt % aqueous sodium hydroxide solution (242 g) was added dropwise at 65–75° C., and the mixture was stirred at the same temperature for 3 h. After confirmation of disappearance of ester compound (methyl 2-cyclohexyl-2-hydroxy-2-phenylacetate) by HPLC, tetrahydrofran and methanol were evaporated under reduced pressure at 65–85° C. Toluene (410 ml) was inpoured, and the aqueous layer was adjusted to pH 1 or below with 7N hydrochloric acid at 60–70° C. The mixture was partitioned by allowing to stand at 70–80° C. and the organic layer was cooled to 0–5° C. The organic layer was aged at the same temperature for 2 h, filtrated, washed with cooled toluene (200 ml) and dried under reduced pressure at 65–75° C. to give the title compound (51.6 g). yield 44.0%, purity 98.6%.

The $^1$H-NMR spectrum data were the same as those obtained in Example 4.

Example 6

2-Cyclohexyl-2-hydroxy-2-phenylacetic acid (Compound [IV], Route 3)

Crude methyl 2-(2'-cyclohexen-1'-yl)-2-hydroxy-2-phenylacetate (61.5 g) obtained on a similar scale to and by the method of Example 1 was dissolved in methanol (287 ml) and 5% palladium carbon (Kawaken Fine Chemicals Co., Ltd., type M, 0.82 g) and 25 wt % aqueous sodium hydroxide solution (50.5 g) were added. The mixture was stirred in a hydrogen gas (1013 kPa) at 60–65° C. for 6 h. 5% Palladium carbon (Kawaken Fine Chemicals Co., Ltd., type M, 0.82 g) was added and the mixture was further stirred under the same conditions for 4 h. The catalyst was filtered off and methanol was evaporated under reduced pressure. The residue was adjusted to pH 1 with 3N hydrochloric acid and toluene (164 ml) was added. The mixture was partitioned by allowing to stand at 60–70° C. and the organic layer was cooled to 0–5° C. The organic layer was aged for 1 h at the same temperature, filtrated, washed with cooled toluene (50 ml) and dried under reduced pressure at 65–75° C. to give the title compound (32.5 g).

yield from methyl benzoylformate: 55.5% purity:98.8%,

The $^1$H-NMR spectrum data were the same as those obtained in Example 4.

Example 7

Methyl 2-cyclohexyl-2-hydroxy-2-phenylacetate (Compound [III])

Crude methyl 2-(2'-cyclohexen-1'-yl)-2-hydroxy-2-phenylacetate (62.8 g) obtained on a similar scale to and by the method of Example 1 was dissolved in methanol (287 ml) and triethylamine (28.7 ml) and 10% palladium carbon (Degussa Japan E106XNN/W, 1.24 g) were added. The mixture was stirred at 40° C. in a hydrogen gas (1520 kPa) for 10 h. After the catalyst was filtered off, methanol was evaporated under reduced pressure and the residue was purified by silica gel column chromatography to give the title compound (40.2 g, yield :64.8%). This was used as the reference standard in Examples 9–16.

$^1$H-NMR(400 MHz, CDCl$_3$) δ=1.02–1.48 (7H, m), 1.58–1.70 (2H, m), 1.75–1.83 (1H, m), 2.18–2.27 (1H, m), 3.68 (1H, s), 3.77 (3H, s), 7.23–7.28 (1H, m), 7.30–7.36 (2H, m), 7.62–7.65 (2H, m) ppm

Example 8

2-Cyclohexyl-2-hydroxy-2-phenylacetic acid (compound [IV])

2-(2'-Cyclohexen-1'-yl)-2-hydroxy-2-phenylacetic acid (20.2 g) obtained in Example 2 was dissolved in methanol (200 ml) and 5% palladium carbon (Kawaken Fine Chemicals Co., Ltd., type M, 1.0 g) was added. The mixture was stirred at 25–30° C. in a hydrogen gas (206 kPa) for 13 h and the catalyst was filtered off. Methanol was evaporated under reduced pressure to give the title compound (20.1 g, yield: 98.5%).

The $^1$H-NMR spectrum data were the same as those obtained in Example 4.

Examples 9–16

Methyl 2-cyclohexyl-2-hydroxy-2-phenylacetate (Compound [III])

Methyl benzoylformate (1.64 g, 10 mmol) and cyclohexene (1.64 g, 20 mmol) were dissolved in a solvent under a nitrogen atmosphere and a Lewis acid was added. The mixture was stirred at the reaction temperature for the reaction time. The solvent, Lewis acid, reaction temperature and reaction time are as shown in Table 1.

The reaction mixture was poured into 6N aqueous hydrochloric acid (12 ml) and partitioned. The organic layer was washed with 10 wt % aqueous sodium carbonate solution (12 ml) and the resulting precipitate was collected by filtration. The organic layer was washed with water (12 ml) and dried over anhydrous magnesium sulfate (0.5 g). The organic layer was concentrated under reduced pressure to give methyl 2-(2'-cyclohexen-1'-yl)-2-hydroxy-2-phenylacetate. The $^1$H-NMR spectrum data were the same as those obtained in Example 1.

Thereto was added methanol (12 ml) and 5% palladium carbon (Kawaken Fine Chemicals Co., Ltd., type M, 0.04 g) was added and the mixture was stirred in a hydrogen gas (350 kPa) for 10 h. The yield of methyl 2-cyclohexyl-2-hydroxy-2-phenylacetate in the solution was calculated by HPLC external standard method using the reference standard (compound obtained in Example 7). The results are as shown in Table 1.

TABLE 1

| | Lewis acid kind amount of use (mmol) | solvent kind amount of use (ml) | reaction temperature (° C.) reaction time (h) | Yield (g) yield (%) |
|---|---|---|---|---|
| Ex. 9 | titanium tetrachloride 15 | Monochlorobenzene 16 | 25–40 9 | 1.61 69.1 |
| Ex. 10 | titanium tetrachloride 15 | 2-chrolotoluene 16 | 60–70 9 | 1.09 46.8 |
| Ex. 11 | titanium tetrachloride 15 | 4-chrolotoluene 16 | 60–70 9 | 1.01 43.5 |
| Ex. 12 | titanium tetrachloride 15 | nitrobenzene 16 | 25–30 9 | 1.21 52.2 |
| Ex. 13 | aluminum chloride 15 | methylene chloride 12 | 25–30 15 | 0.75 32.2 |
| Ex. 14 | aluminum chloride 15 | Monochlorobenzene 16 | 25–30 15 | 0.37 15.8 |
| Ex. 15 | ferric chloride 15 | methylene chloride 12 | 25–30 15 | 0.28 12.1 |
| Ex. 16 | zirconium tetrachloride 15 | Monochlorobenzene 12 | 25–30 9 | 0.05 2.2 |

Example 17

2-Cyclohexyl-2-hydroxy-2-phenylacetic acid (Compound [IV], Route 3)

To a solution of titanium tetrachloride (11.5 kg, 61 mol) in monochlorobenzene (28.5 L) was added dropwise at 35–45° C. over 5 h under a nitrogen atmosphere, a mixture of methyl benzoylformate (9.5 kg, 58 mol) and cyclohexene (9.5 kg, 116 mol). The reaction mixture was stirred at 35–45° C. for 9 h and added dropwise to 11% hydrochloric acid (20.9 kg) at 15–40° C. The mixture after hydrolysis was heated to 55° C. and the aqueous layer was separated. After washing with 35% hydrochloric acid (10.2 kg), the aqueous layer was separated. The organic layer was concentrated under reduced pressure until the inert temperature reached 85° C. at 4 kPa. Water (4.8 kg) was added and evaporated again under reduced pressure. To the residue was added methanol (14.3 L), and then was added 26% aqueous sodium hydroxide solution (0.2 kg) to retain a 40% aqueous methanol solution (25.8 kg) of methyl 2-(2'-cyclohexen-1'-yl)-2-hydroxy-2-phenylacetate.

A half amount (12.9 kg) of the 40% aqueous methanol solution (25.8 kg) of methyl 2-(2'-cyclohexen-1'-yl)-2-hydroxy-2-phenylacetate thus obtained was measured, and methanol (2.4 L) was added thereto. The mixture was heated to 67° C., and 26% aqueous sodium hydroxide solution (8.8 kg) was added dropwise at 65–80° C. After the completion of the dropwise addition, the mixture was heated as it was in an autoclave, and stirred at 130° C., 0.45 Mpa for 3 h. The reaction mixture was cooled to 60° C. and adjusted to pH 5.5 with 30% sulfuric acid (4.7 kg). The reaction mixture was heated to 60° C. Active charcoal (0.5 kg) and 5% palladium carbon (N.E. CHEMCAT CORPORATION NX-Type, wet amount 0.4 kg, dry amount 0.2 kg) were added and the inside of the system was thoroughly substituted with nitrogen. Then, the inside of the system was substituted with hydrogen and hydrogen was fed according to absorption, thereby raising the final pressure from 101 kPa to 800 kPa, and the mixture was maintained further at 800 kPa, 60° C. for 2 h. The inside of the system was substituted with nitrogen, and the catalyst and active charcoal were filtered off. The residue was washed with a mixture (11 kg) of methanol-water (2:1). The filtrate and washing were combined to give a 30% aqueous methanol solution (36.8 kg) of sodium 2-cyclohexyl-2-hydroxy-2-phenylacetate.

The remaining half amount of the 40% aqueous methanol solution of methyl 2-(2'-cyclohexen-1'-yl)-2-hydroxy-2-phenylacetate was treated in the same manner to give a 30% aqueous methanol solution (37.4 kg) of sodium 2-cyclohexyl-2-hydroxy-2-phenylacetate. The solvent was evaporated from the thus-obtained aqueous methanol solution (74.2 kg) of sodium 2-cyclohexyl-2-hydroxy-2-phenylacotate at atmospheric pressure at an inert temperature of 86° C. To the residue was added toluene (57 L), and then was added 18% sulfuric acid (15.8 kg) at around 70° C. to adjust the mixture to pH 1. After stirring and standing of the mixture, the aqueous layer was removed by partitioning. To the organic layer were added toluene (9.5 L), warm water (19 L) and 28% aqueous ammonia (0.4 kg), and after stirring and standing, the aqueous layer was removed by partitioning. The organic layer was partitioned twice and washed with warm water (19 L) at 70° C. twice. Toluene (ca. 10 L) was evaporated under reduced pressure at an inert temperature of 85–95° C. The mixture was heated to 95° C. to completely dissolve crystals. The solution was cooled to 5° C. over about 8 h, and the resulting crystals were collected by filtration and dried to give the title compound (yield: 7.72 kg, yield :58.5%, purity: 99.8%).

Example 18

Optically active 2-cyclohexyl-2-hydroxy-2-phenylacetic acid

To a solution of benzoylformic acid (9.0 g) in toluene (135 ml) was added thionyl chloride (8.2 g) and the reaction mixture was stirred at 75° C. for 2 h. A solution, from which about 40 ml of the solvent had been evaporated under reduced pressure, was added dropwise to a solution of (S)-methyl lactate (7.1 g) and triethylamine (6.6 g) in toluene (60 ml) at 2–5° C. and the mixture was stirred at 20° C. for 14 h. Water (135 ml) was added to the mixture and the mixture was partitioned. The organic layer was washed successively with 10% aqueous sodium carbonate solution, water and saturated brine, and the organic solvent was evaporated to give methyl (S)-2-(benzoylformyloxy)propionate (7.6 g).

The obtained methyl (S)-2-(benzoylformyloxy)propionate (7.4 g) was dissolved in monochlorobenzene (74 ml), and cyclohexene (5.2 g) and titanium tetrachloride (7.8 g) were added. The reaction mixture was stirred at 20–25° C. for 15 h. The reaction mixture was poured into 6N hydrochloric acid (74 ml) and extracted with toluene (37 ml). The extract was washed with 6N hydrochloric acid (37 ml). To the organic layer were added 25% aqueous sodium hydroxide solution (20 g) and methanol (74 ml) and the reaction mixture was stirred at 60–65° C. for 2 h. Water (74 ml) and toluene (74 ml) were added to the reaction mixture and the partitioned organic layer was combined with the extract obtained by extracting the aqueous layer again with toluene (74 ml) and concentrated. 6N Hydrochloric acid (29 g) was added to the concentrated residue and the mixture was extracted with ethyl acetate (74 ml). The organic layer was washed with water and concentrated to give a diastereomer mixture (5.2 g) of crude optically active 2-(2'-cyclohexen-1'-yl)-2-hydroxy-2-phenylacetic acid. This (4.1 g) was dissolved in methanol (40 ml) and 5% palladium carbon (Kawaken Fine Chemicals Co., Ltd., type M, 3 g) was added. The mixture was stirred at atmospheric pressure in a hydrogen gas for 15 min. The catalyst was filtered off and the solvent was evaporated. The residue was purified by silica gel column chromatography (eluent: toluene/ethyl acetate) to give the title compound (3.3 g, yield from benzoylformic acid: 31%). This was amidated with (S)-phenylethylamine by a conventional method and the optical purity was measured by HPLC, which was found to be 22% e.e.

Example 19

In the same manner as in Example 18 except that (L)-(+)-diethyl tartrate was used at 1/2 molar ratio instead of (S)-methyl lactate, (2R,3R)-diethyl bis(benzoylformyloxy)-butanedionate was synthesized, from which the title compound as obtained (yield from benzoylformic acid: 20%). This was midated with (S)-phenylethylamine by a conventional method and the optical purity was measured by HPLC, which was found to be 36% e.e.

According to the present invention, novel 2-(2'-cyclohexen-1'-yl)-2-hydroxy-2-phenylacetic acid ester (compound [II]), obtained by reacting cyclohexene and benzoylformic acid ester in the presence of a Lewis acid, is used as an intermediate and hydrolyzed and reduced to give 2-cyclohexyl-2-hydroxy-2-phenylacetic acid useful as an intermediate for pharmaceutical products, by an industrial method, economically, safely and in a good yield.

This application is based on a patent application No. 2000-339437 filed in Japan, the contents of which are hereby incorporated by reference.

What is claimed is:

1. A compound of the formula [II]

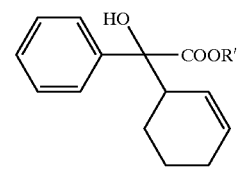

wherein R' is (a) linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and (α-(2-cyclohexen-1-yl)-α-hydroxy-benzyl)carbonyloxy, or (b) cyclohexyl, cyclopentyl or norbornyl, each of which is optionally substituted by at least one substituent selected from the group consisting of linear or branched chain alkyl having 1 to 15 carbon atom(s) and phenyl, or an optically active form thereof 2. The compound of claim 1, wherein R' is (a) linear or branched chain alkyl having 1 to 15 carbon atom(s), which is optionally substituted by at least one substituent selected from the group consisting of phenyl, naphthyl, cyclohexyl, cyclopentyl and norbornyl, or (b) cyclohexyl, cyclopentyl or norbornyl, each of which is optionally substituted by at least one substituent selected from the group consisting of linear or branched chain alkyl having 1 to 15 carbon atom(s) and phenyl, or an optically active form thereof.

3. A method for producing a compound of claim 1, which method comprising reacting a compound the formula [I]

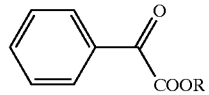
[I]

wherein R is
(a) linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and beuzoylcarbonyloxy, or
(b) cyclohexyl, cyclopentyl or norbornyl, each of which is optionally substituted by at least one substituent selected from the group consisting of linear or branched chain alkyl having 1 to 15 carbon atom(s) and phenyl or an optically active form thereof, with cyclohexene in the presence of a Lewis acid.

4. The production method of claim 3, wherein R and R' are each
(a) linear or branched chain alkyl having 1 to 15 carbon atom(s), which is optionally substituted by at least one substituent selected from the group consisting of phenyl, naphthyl, cyclohexyl, cyclopentyl and norbornyl, or
(b) cyclohexyl, cyclopentyl or norbornyl, each of which is optionally substituted by at least one substituent selected from the group consisting of linear or branched chain alkyl having 1 to 15 carbon atom(s) and phenyl.

5. The production method of claim 3, wherein R and R' are each a group having an asymmetric carbon atom.

6. The production method of claim 3, wherein the Lewis acid is an optically active Lewis acid having an asymmetric ligand.

7. The production method of claim 3, wherein the Lewis acid is titanium tetrachloride.

8. The production method of claim 3, wherein the reaction is carried out in monochlorobenzene.

9. A method for producing a compound of the formula [III]

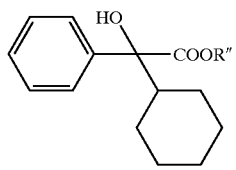
[III]

wherein R" is
(a) linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and (α-cyclohexyl-α-hydroxybenzyl)carbonyloxy, or
(b) cyclohexyl, cyclopentyl or norbornyl, each of which is optionally substituted by at least one substituent selected from the group consisting of linear or branched chain alkyl having 1 to 15 carbon atom(s) and phenyl or an optically active form, which method comprises reducing a compound of claim 1.

10. The production method of claim 9, wherein R' and R" are each
(a) linear or branched chain alkyl having 1 to 15 carbon atom(s), which is optionally substituted by at least one substituent selected from the group consisting of phenyl, naphthyl, cyclohexyl, cyclopentyl and norbornyl, or
(b) cyclohexyl, cyclopentyl or norbornyl, each of which is optionally substituted by at least one substituent selected from the group consisting of linear or branched chain alkyl having 1 to 15 carbon atom(s) and phenyl.

11. A method for producing a compound of the formula [V]

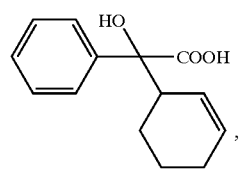
[V]

an optically active form thereof or a salt thereof, which method comprises hydrolyzing a compound of claim 1.

12. The production method of claim 11, wherein R' is
(a) linear or branched chain alkyl having 1 to 15 carbon atom(s), which is optionally substituted by at least one substituent selected from the group consisting of phenyl, naphthyl, cyclohexyl, cyclopentyl and norbornyl, or
(b) cyclohexyl, cyclopentyl or norbornyl, each of which is optionally substituted by at least one substituent selected from the group consisting of linear or branched chain alkyl having 1 to 15 carbon atom(s) and phenyl.

13. A method for producing 2-cyclohexyl-2-hydroxy-2-phenylacetic acid of the formula [IV]

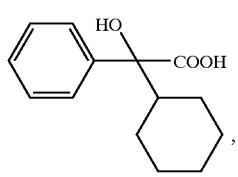
[IV]

an optically active form thereof or a salt thereof, which method comprises subjecting a compound of claim 1 to hydrolysis and reduction.

14. The production method of claim 13, wherein R' is
(a) linear or branched chain alkyl having 1 to 15 carbon atom(s), which is optionally substituted by at least one substituent selected from the group consisting of phenyl, naphthyl, cyclohexyl, cyclopentyl and norbornyl, or
(b) cyclohexyl, cyclopentyl or norbornyl, each of which is optionally substituted by at least one substituent selected from the group consisting of linear or branched chain alkyl having 1 to 15 carbon atom(s) and phenyl.

15. The production method of claim 13, which comprises simultaneous hydrolysis and reduction.

16. The production method of claim 13, which comprises hydrolysis after reduction.

17. The production method of claim 13, which comprises reduction after hydrolysis.

18. A method for producing a compound of the formula [III]

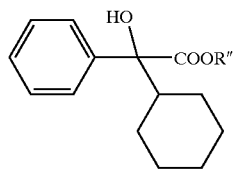

wherein R" is (a) linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and (α-cyclohexyl-α-hydroxybenzyl)carbonyloxy, or (b) cyclohexyl, cyclopentyl or norbornyl, each of which is optionally substituted by at least one substituent selected from the group consisting of linear or branched chain alkyl having 1 to 15 carbon atom(s) and phenyl or an optically active form thereof, which method comprising reacting a compound the formula [I]

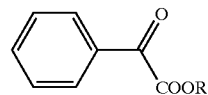

wherein R is (a) linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and benzoylcarbonyloxy, or (b) cyclohexyl, cyclopentyl or norbornyl, each of which is optionally substituted by at least one substituent selected from the group consisting of linear or branched chain alkyl having 1 to 15 carbon atom(s) and phenyl or an optically active form thereof, with cyclohexene in the presence of a Lewis acid to give a compound of claim 1, and reducing the same.

19. The production method of claim 18, wherein R, R' and R" are each (a) linear or branched chain alkyl having 1 to 15 carbon atom(s), which is optionally substituted by at least one substituent selected from the group consisting of phenyl, naphthyl, cyclohexyl, cyclopentyl and norbornyl, or (b) cyclohexyl, cyclopentyl or norbornyl, each of which is optionally substituted by at least one substituent selected from the group consisting of linear or branched chain alkyl having 1 to 15 carbon atom(s) and phenyl.

20. A method for producing a compound of the formula [VI]

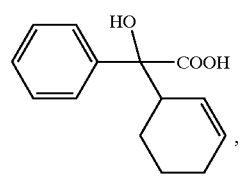

an optically active form thereof or a salt thereof, which method comprises reacting a compound of the formula [I]

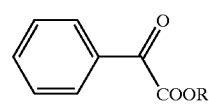

wherein R is (a) linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and benzoylcarbonyloxy, or (b) cyclohexyl, cyclopentyl or norbornyl, each of which is optionally substituted by at least one substituent selected from the group consisting of linear or branched chain alkyl having 1 to 15 carbon atom(s) and phenyl or an optically active form thereof, with cyclohexene in the presence of a Lewis acid to give a compound of claim 1 and hydrolyzing the same.

21. The production method of claim 20, wherein R and R' are each (a) linear or branched chain alkyl having 1 to 15 carbon atom(s), which is optionally substituted by at least one substituent selected from the group consisting of phenyl, naphthyl, cyclohexyl, cyclopentyl and norbornyl, or (b) cyclohexyl, cyclopentyl or norbornyl, each of which is optionally substituted by at least one substituent selected from the group consisting of linear or branched chain alkyl having 1 to 15 carbon atom(s) and phenyl.

22. A method of producing 2-cyclohexyl-2-hydroxy-2-phenylacetic acid of the formula [IV]

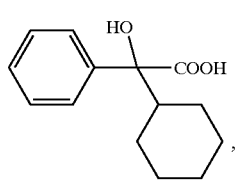

an optically active form thereof or a salt thereof, which method comprises reacting a compound of the formula [I]

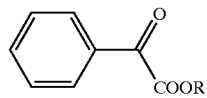

wherein R is
(a) linear or branched chain alkyl having 1 to 15 carbon atom(s), which is optionally substituted by at least one substituent selected from the group consisting of phenyl, naphthyl, cyclohexyl, cyclopentyl, norbornyl, methoxycarbonyl, ethoxycarbonyl and benzoylcarbonyloxy, or
(b) cyclohexyl, cyclopentyl or norbornyl, each of which is optionally substituted by at least one substituent selected from the group consisting of linear or branched chain alkyl having 1 to 15 carbon atom(s) and phenyl or an optically active form thereof, with cyclohexene in the presence of a Lewis acid to give a compound of claim 1, and subjecting the same to hydrolysis and reduction.

23. The production method of claim 22, wherein R and R' are each
(a) linear or branched chain alkyl having 1 to 15 carbon atom(s), which is optionally substituted by at least one substituent selected from the group consisting of phenyl, naphthyl, cyclohexyl, cyclopentyl and norbornyl, or
(b) cyclohexyl, cyclopentyl or norbornyl, each of which is optionally substituted by at least one substituent selected from the group consisting of linear or branched chain alkyl having 1 to 15 carbon atom(s) and phenyl.

24. The production method of claim 22, which comprises simultaneous hydrolysis and reduction.

25. The production method of claim 22, which comprises hydrolysis after reduction.

26. The production method of claim 24, which comprises reduction after hydrolysis.

* * * * *

UNITED STATES PATENT AND TRADEMARK OFFICE
CERTIFICATE OF CORRECTION

PATENT NO. : 6,777,576 B2
DATED : August 17, 2004
INVENTOR(S) : Ikemoto et al.

It is certified that error appears in the above-identified patent and that said Letters Patent is hereby corrected as shown below:

Column 25,
Line 16, "beuzoylcarbonyloxy" should read -- benzoylcarbonyloxy --.

Signed and Sealed this

First Day of March, 2005

JON W. DUDAS
*Director of the United States Patent and Trademark Office*